US009430805B2

(12) United States Patent
Bulat

(10) Patent No.: US 9,430,805 B2
(45) Date of Patent: Aug. 30, 2016

(54) SYSTEM AND METHOD FOR DELIVERING MEDICAL EXAMINATION, TREATMENT AND ASSISTANCE OVER A NETWORK

(71) Applicant: American Doctors On-Line, Inc., North Dartmouth, MA (US)

(72) Inventor: Paul I. Bulat, Brewster, MA (US)

(73) Assignee: American Doctors Online, Inc., Dartmouth, MA (US)

( * ) Notice: Subject to any disclaimer, the term of this patent is extended or adjusted under 35 U.S.C. 154(b) by 258 days.

(21) Appl. No.: 13/952,913

(22) Filed: Jul. 29, 2013

(65) Prior Publication Data

US 2013/0307918 A1    Nov. 21, 2013

Related U.S. Application Data

(60) Continuation of application No. 11/409,713, filed on Apr. 24, 2006, now Pat. No. 9,269,116, which is a continuation-in-part of application No. 11/321,332, filed on Dec. 29, 2005, now Pat. No. 7,691,059, which is a division of application No. 10/694,519, filed on Oct. 27, 2003, now Pat. No. 7,011,629, which is a continuation-in-part of application No. 09/855,738, filed on May 14, 2001, now Pat. No. 6,638,218.

(51) Int. Cl.
*A61B 5/00* (2006.01)
*G06F 19/00* (2011.01)
*G06Q 50/22* (2012.01)
*H04N 7/14* (2006.01)

(52) U.S. Cl.
CPC .............. *G06Q 50/22* (2013.01); *A61B 5/0002* (2013.01); *A61B 5/411* (2013.01); *H04N 7/141* (2013.01)

(58) Field of Classification Search
CPC ...... G06Q 50/22; H04N 7/141; A61B 5/411; A61B 5/0002
See application file for complete search history.

(56) References Cited

U.S. PATENT DOCUMENTS 4,259,548 A    3/1981  Fahey et al. .................. 179/5 R
4,805,209 A *  2/1989  Baker, Jr. ........... H04Q 11/0407
                                                        379/212.01

(Continued)

OTHER PUBLICATIONS

U.S. Appl. No. 11/409,713, filed Apr. 24, 2006.

(Continued)

*Primary Examiner* — William Thomson
*Assistant Examiner* — Shirley Jian
(74) *Attorney, Agent, or Firm* — Sunstein Kann Murphy & Timbers LLP

(57) ABSTRACT

A system for delivering medical examination, diagnosis, and treatment services includes a plurality of health care practitioner terminals, each having a display device, a plurality of patient terminals in audiovisual communication with any of the health care practitioner terminals, a call center, in communication with the patient terminals and the health care practitioner terminals, routing a call from a patient at one of the patient terminals to an available health care practitioner at one of the health care practitioner terminals, so that the available health care practitioner may carry on a two-way conversation with the patient and visually observe the patient, and a protocol database containing a plurality of protocol segments such that a relevant segment of the protocol may be displayed in real time on the display device of the health care practitioner terminal for use by the available health care practitioner in making an assessment of the patient.

10 Claims, 8 Drawing Sheets

(56) References Cited

U.S. PATENT DOCUMENTS

| | | | | |
|---|---|---|---|---|
| 4,942,602 A | * | 7/1990 | Baker, Jr. | H04M 3/51 370/270 |
| 4,943,996 A | * | 7/1990 | Baker, Jr. | H04M 3/51 379/201.04 |
| 5,005,126 A | | 4/1991 | Haskin | 364/413.13 |
| 5,319,355 A | | 6/1994 | Russek | 340/573 |
| 5,434,611 A | | 7/1995 | Tamura | 348/8 |
| 5,441,047 A | | 8/1995 | David et al. | 128/670 |
| 5,495,284 A | * | 2/1996 | Katz | 348/14.09 |
| 5,544,649 A | * | 8/1996 | David et al. | 600/301 |
| 5,558,638 A | | 9/1996 | Evers et al. | 604/66 |
| 5,619,991 A | | 4/1997 | Sloane | 128/630 |
| 5,687,734 A | | 11/1997 | Dempsey et al. | 128/696 |
| 5,810,747 A | | 9/1998 | Brudny et al. | 600/595 |
| 5,911,687 A | | 6/1999 | Sato et al. | 600/300 |
| 5,926,476 A | * | 7/1999 | Ghaibeh | H04L 12/2801 370/395.65 |
| 5,960,411 A | | 9/1999 | Hartman et al. | 705/26 |
| 5,987,519 A | | 11/1999 | Peifer et al. | 709/230 |
| 6,007,459 A | | 12/1999 | Burgess | 482/4 |
| 6,021,428 A | * | 2/2000 | Miloslavsky | 709/206 |
| 6,157,401 A | | 12/2000 | Wiryaman | 348/15 |
| 6,168,563 B1 | | 1/2001 | Brown | 600/301 |
| 6,195,683 B1 | | 2/2001 | Palmer et al. | 709/204 |
| 6,205,716 B1 | | 3/2001 | Peltz | 52/36.2 |
| 6,206,829 B1 | | 3/2001 | Iliff | 600/300 |
| 6,208,372 B1 | | 3/2001 | Barraclough | 348/14.16 |
| 6,215,515 B1 | | 4/2001 | Voois et al. | 348/14 |
| 6,219,087 B1 | * | 4/2001 | Uiterwyk et al. | 348/14.08 |
| 6,259,355 B1 | | 7/2001 | Chaco et al. | 340/286.07 |
| 6,263,049 B1 | * | 7/2001 | Kuhn | 379/32.01 |
| 6,278,999 B1 | | 8/2001 | Knapp | 707/9 |
| 6,302,844 B1 | | 10/2001 | Walker et al. | 600/300 |
| 6,369,847 B1 | | 4/2002 | James et al. | 348/14.01 |
| 6,373,836 B1 | * | 4/2002 | Deryugin et al. | 370/352 |
| 6,471,087 B1 | | 10/2002 | Shusterman | 221/2 |
| 6,482,156 B2 | | 11/2002 | Iliff | 600/300 |
| 6,572,543 B1 | | 6/2003 | Christopherson et al. | 600/300 |
| 6,581,105 B2 | * | 6/2003 | Miloslavsky et al. | 709/238 |
| 6,584,445 B2 | | 6/2003 | Papageorge | 705/3 |
| 6,597,685 B2 | * | 7/2003 | Miloslavsky et al. | 370/352 |
| 6,625,139 B2 | * | 9/2003 | Miloslavsky et al. | 370/352 |
| 6,638,218 B2 | * | 10/2003 | Bulat | 600/300 |
| 6,662,032 B1 | | 12/2003 | Gavish et al. | 600/323 |
| 6,731,324 B2 | | 5/2004 | Levy | 348/14.08 |
| 6,893,407 B1 | | 5/2005 | Brooks et al. | 600/595 |
| 7,011,629 B2 | * | 3/2006 | Bulat | 600/300 |
| 7,185,282 B1 | | 2/2007 | Naidoo et al. | 715/718 |
| 7,315,825 B2 | | 1/2008 | Rosenfeld et al. | 705/2 |
| 7,612,679 B1 | * | 11/2009 | Fackler et al. | 340/573.1 |
| 7,653,557 B2 | | 1/2010 | Sweetser | 705/3 |
| 7,691,059 B2 | * | 4/2010 | Bulat | 600/300 |
| 7,720,692 B2 | | 5/2010 | Glimp et al. | 705/2 |
| 7,835,926 B1 | * | 11/2010 | Naidoo et al. | 705/2 |
| 7,870,006 B2 | | 1/2011 | Tkaczyk et al. | 705/2 |
| 7,970,633 B2 | * | 6/2011 | Bulat | 705/3 |
| 8,112,293 B2 | | 2/2012 | Howell et al. | 705/3 |
| 2002/0186243 A1 | | 12/2002 | Ellis et al. | 345/753 |
| 2003/0028399 A1 | * | 2/2003 | Davis et al. | 705/2 |
| 2003/0126593 A1 | | 7/2003 | Mault | 725/10 |
| 2006/0106290 A1 | | 5/2006 | Bulat | 600/300 |
| 2006/0173708 A1 | | 8/2006 | Vining et al. | 705/2 |
| 2006/0293572 A1 | | 12/2006 | Bulat | 600/300 |
| 2009/0083066 A1 | | 3/2009 | Bailey et al. | 705/2 |

OTHER PUBLICATIONS

U.S. Appl. No. 12/870,341, filed Aug. 27, 2010.

* cited by examiner

SYSTEM AND METHOD FOR DELIVERING MEDICAL EXAMINATION, TREATMENT AND ASSISTANCE OVER A NETWORK

CROSS REFERENCE TO RELATED APPLICATIONS

The present application is a continuation of U.S. patent application Ser. No. 11/409,713 filed Apr. 24, 2006, which is a continuation-in-part of U.S. patent application Ser. No. 11/321,332, filed Dec. 29, 2005, which is a divisional application of U.S. patent application Ser. No. 10/694,519, filed Oct. 27, 2003, now U.S. Pat. No. 7,011,629, which is a continuation-in-part of U.S. patent application Ser. No. 09/855,738, filed May 14, 2001, now U.S. Pat. No. 6,638,218. The above-referenced patents and patent application are hereby incorporated by reference in their entirety.

FIELD OF THE INVENTION AND BACKGROUND ART

The present invention relates to medical examination, diagnosis and treatment, and more particularly, to providing such services over a network.

Health care costs in the United States exceed one trillion dollars per year. In 1996, spending on health care in the United States exceeded fourteen percent of the Gross Domestic Product. Current health care system costs include annual service to over ninety million people in over five thousand hospital emergency departments. These ninety million or more visits impose an enormous burden on emergency departments. Ambulances on route toward the closest available emergency department are often diverted to other hospitals, sometimes located in another city. The cause of such calamities is multi-factorial and includes: nursing shortages, bed unavailability, and grossly overcrowded, overburdened emergency rooms.

Telecommunications technologies, and in particular, video-conferencing, offer an opportunity to provide cost effective care in a variety of settings. In particular, tele-medicine and tele-healthcare have been envisioned with respect to many specialties including: pathology, dermatology, surgery, opthamology, cardiology, and radiology. However, diagnosis and treatment in these areas require either a human presenter or mechanical equipment at the patient end to gather pertinent information related to the patient's condition.

For example, it is known in the prior art to provide remote monitoring of patients over a network. U.S. Pat. No. 5,544,646, which is hereby incorporated herein, issued to David et al., discloses an interactive television and audio patient monitoring system for connecting a patient situated at home or in a hospital room with a central monitoring station that is manned by one or more health care practitioners. The invention provides two-way interactive visual communications between a patient and a health care practitioner via cable television lines whereby the central station may continuously monitor one or more medical parameters (such as, ECG, blood pressure, respiration, etc.) by utilizing medical equipment located in the patient's hospital room or home.

Similarly, U.S. Pat. No. 5,810,747, issued to Brudny et al., and also incorporated herein by reference, discloses an interactive training system used for monitoring a patient suffering from neurological disorders of movement. The system includes a patient station that includes a computer in communication with a supervisor station via a local area network or the Internet. Sensors collect physiologic information and physical information from the patient while the patient is undergoing training. This information is provided to the supervisor station to be summarized and displayed to the patient and the supervisor.

U.S. Pat. No. 6,168,563, issued to Brown and incorporated herein by reference, discloses a system and method for enabling a health care provider to monitor and manage a health condition of a patient. The system includes a health care provider apparatus operated by a health care provider and a remotely programmable patient apparatus that is operated by a patient. The health care provider develops a script program using the health care provider apparatus and sends the script program to the remotely programmable patient apparatus through a communication network such as the World Wide Web. The script program is computer executable, and provides information to the patient about the patient's health condition by asking the patient questions and receiving answers to the questions. The answers are forwarded to the health care provider through the communication network and processed for further management of the patient's health condition by the health care provider. The patient data may also include information supplied by a physiological monitoring device that is connected to the remotely programmable patient apparatus.

In addition, U.S. Pat. No. 6,205,716, issued to Peltz and also incorporated herein by reference, discloses a secure, modular interactive two-way tele-collaborative video conferencing and imaging enclosure for remotely monitoring physiological attributes of a user by medical specialists and remote interaction between users and medical specialists. Access to the system requires participation in a healthcare program or health insurance program, such as an HMO. The healthcare program provides the patient with an "access card" that enables the patient to use the enclosure.

SUMMARY OF THE INVENTION

In accordance with a first embodiment of the invention, method for providing a covering physician service via a network includes informing a patient of a practicing physician of the availability of the plurality of patient terminals and referring the patient to one of the patient terminals upon agreement of the patient. A call from the patient at the patient terminal is received at a call center, the call center enabling any of a first plurality of physician terminals to be in audio-visual communication over the network with any of a second plurality of patient terminals, and the call is routed to an available physician at one of the physician terminals so that the available physician may carry on a two-way conversation with the patient and visually observe the patient. The available physician is permitted to make an assessment of the patient and to treat the patient.

In accordance with a related embodiment, the method may further include receiving information related to the patient at the physician terminal via the network and/or forwarding information related to the patient to the practicing physician via the network following interaction of the patient with the available physician. Similarly, the method may include forwarding information related to the patient to a health care management system associated with the physician. The health care management system may be a healthcare management organization, a point of service health care system, or a preferred provider organization.

In accordance with another embodiment of the invention, a method for providing a covering physician service via a network includes informing a patient of a practicing physician of the availability of the plurality of patient terminals and referring the patient to one of the patient terminals upon agreement of the patient. A call from the patient at the patient terminal is received at a call center, the call center enabling any of a first plurality of health care practitioner terminals to be in audio-visual communication over the network with any of a second plurality of patient terminals. The call is routed to an available health care practitioner at one of the health care practitioner terminals so that the available health care practitioner may carry on a two-way conversation with the patient and visually observe the patient. The available health care practitioner is then permitted to make an assessment of the patient and to treat the patient.

In accordance with a related embodiment, information related to the patient may be received at the health care practitioner terminal via the network and/or information related to the patient may be forwarded to the practicing physician via the network following interaction of the patient with the available physician. Similarly, information related to the patient may be forwarded to a health care management system associated with the physician. The health care management system may be a healthcare management organization, a point of service health care system or a preferred provider organization. The health care practitioner may be a nurse practitioner or an internist.

In accordance with a further embodiment of the invention, a method for delivering medical examination, diagnosis, and treatment services from a physician to a patient over a network includes providing a call center enabling any of a first plurality of health care practitioner terminals to be in audiovisual communication over the network with any of a second plurality of patient terminals. A call is received at the call center from a patient at one of the patient terminals routed to an available health care practitioner at one of the health care practitioner terminals such that the available health care practitioner may carry on a two-way conversation with the patient and visually observe the patient. The available health care practitioner is permitted to make an assessment of the patient and to conduct an examination of the patient over the network, including by a visual study of the patient.

In accordance with a related embodiment, the method may also include having the patient stand in the course of the examination, so as to provide a basis for a gross evaluation of patient condition. In accordance with another related embodiment, making an assessment may include making an assessment in accordance with a protocol. In accordance with further related embodiments, providing a call center enabling any of a first plurality of heath care practitioner terminals to be in audiovisual communication over the network with any of a second plurality of patient terminals may include providing a second plurality of patient terminals such that unrestricted access to one or more of the patient terminals is permitted and/or receiving a call at the call center from a patient may include providing a telephone in one or more of the patient terminals that permits direct access to the call center upon lifting the receiver. In accordance with other related embodiments, making an assessment in accordance with the protocol may include making an assessment in accordance with a protocol stored in a database and/or making an assessment in accordance with the protocol may include displaying in real time a relevant segment of the protocol to the available physician. Similarly, permitting the physician to prescribe a treatment may include permitting the physician to refer the patient to a third party for treatment and/or referring the patient to a third party for treatment may include referring the patient to one or more of a primary care physician, specialist, hospital, emergency room, ambulance service or clinic. Referring the patient to a third party may additionally include communicating with the third party via an electronic link included in a relevant segment of a protocol stored in a protocol database resident on a digital storage medium and the electronic link may be a hypertext link.

In accordance with further related embodiments, permitting the physician to prescribe a treatment may include, when a treatment is being prescribed by a physician, communicating a prescription over the network to a pharmacy and/or communicating the prescription over the network to the pharmacy may include communicating to the pharmacy instructions to be given to the patient pertaining to the treatment of the patient. Communicating the prescription over the network to the pharmacy may also include communicating the prescription to the pharmacy via a hypertext link included in a relevant segment of a protocol stored in a database resident on a digital storage medium. In accordance with another related embodiment, permitting the physician to conduct the examination may be accomplished under conditions such that the examination is conducted without medical instruments at the patient terminal where the patient is located.

In accordance with another embodiment of the invention, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. A call center is in communication with the patient terminals and the health care practitioner terminals, the call center routing a call from a patient at one of the patient terminals to an available health care practitioner at one of the health care practitioner terminals, so that the available health care practitioner may carry on a two-way conversation with the patient and visually observe the patient. A protocol database resident on a digital storage medium is accessible to each of the health care practitioner terminals. The protocol database contains a plurality of protocol segments such that a relevant segment of the protocol may be displayed in real time on the display device of the health care practitioner terminal of the available health care practitioner for use by the available health care practitioner in making an assessment of the patient.

In accordance with related embodiments, the relevant segment of the protocol displayed in real time on the display device of the health care practitioner terminal may include an electronic link that establishes communication between the available health care practitioner and a third party and the third party may be one or more of a primary care physician, specialist, hospital, emergency room, ambulance service, clinic or pharmacy. The electronic link may be a hypertext link.

In accordance with further related embodiments, the system may also include a patient database accessible to each of the health care practitioner terminals for storing patient information and the patient information may be displayed on the display device of the health care practitioner terminal of the available health care practitioner. Similarly, the system may include a medication database accessible to each of the physician terminals for storing medication information. Additionally, each patient terminal may be configured to permit the available health care practitioner to conduct an examination of the patient, including by visual observation of the patient, while the patient is standing.

In accordance with other related embodiment, the patient terminals may include a telephone such that a patient may establish a direct connection to the call center by picking up the telephone receiver. Further, the protocol database may be resident on a server that is in communication with each of the health care practitioner terminals and each of the health care practitioner terminals may include a local storage device and the protocol database is replicated on the local storage device of one or more of the physician terminals.

In accordance with yet another embodiment of the invention, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. A call center is in communication with the patient terminals and the health care practitioner terminals. The call center routes a call from a patient at one of the patient terminals to an available health care practitioner at one of the health care practitioner terminals, so that the available health care practitioner may carry on a two-way conversation with the patient and visually observe the patient.

In accordance with a further embodiment of the invention, a system for delivering medical examination, diagnosis, and treatment services from a physician to a patient over a network includes a first plurality of health care practitioner terminals, each of the first plurality of health care practitioner terminals including a display device and a second plurality of patient terminals in audiovisual communication over a network with any of the first plurality of health care practitioner terminals. Each of the second plurality of patient terminals includes a camera having pan, tilt and zoom modes, such modes being controlled from the first plurality of health care practitioner terminals. A call center is in communication with the patient terminals and the health care practitioner terminals and the call center routes a call from a patient at one of the patient terminals to an available health care practitioner at one of the health care practitioner terminals, so that the available health care practitioner may carry on a two-way conversation with the patient and visually observe the patient.

In accordance with a further embodiment of the invention, a method for delivering medical examination, diagnosis, and treatment services to a patient over a network includes providing a call center enabling any of a plurality of health care practitioner terminals to be in audiovisual communication over the network with any of a plurality of patient terminals. A call at the call center initiated by a person at one of the patient terminals is received and the call is routed to an available health care practitioner at one of the health care practitioner terminals, so that the available health care practitioner may carry on a two-way conversation with the person and visually observe the patient, wherein the person is the patient, a family member of the patient, and/or a second health care practitioner. The available health care practitioner is permitted to make an assessment of the patient and to conduct an examination of the patient over the network, including by a visual study of the patient.

In accordance with a related embodiment, the method may also include providing medical information of the patient to the available health care practitioner. Any of a plurality of patient terminals may include portable patient terminals capable of wireless communication. Receiving a call at the call center initiated by a person may include providing a communication connection in one or more of the patient terminals that permits direct access to the call center upon establishing the communication connection. In accordance with another related embodiment, the method may also include permitting the available health care practitioner to prescribe a treatment. Permitting the available health care practitioner to prescribe a treatment may include referring the patient to a third party, where the third party is a primary care physician, a specialist, a hospital, an emergency room, an ambulance service, and/or a clinic. Referring the patient to a third party may include communicating with the third party via an electronic link included in a relevant segment of a protocol stored in a protocol database resident on a digital storage medium. The available health care practitioner may be a physician, a nurse practitioner or a physician's assistant, and permitting the available health care practitioner to prescribe a treatment may include communicating a prescription over the network to a pharmacy. Communicating the prescription over the network to the pharmacy may include communicating to the pharmacy instructions to be given to the patient pertaining to the treatment of the patient. Permitting the available health care practitioner to prescribe a treatment may include prescribing a treatment order, where the treatment order is an inhalation therapy order, an oxygen order, a laboratory order, a radiology order, a consultation order, an orthopedic hardware order, a diet order, an intravenous fluid order, an activity order, a vital sign order, an intake order, an output order, a diagnostic test order, a rehabilitation order, and/or a supportive therapy order.

In accordance with a further embodiment of the invention, a method for delivering medical examination, diagnosis, and treatment services over a network to a patient in a skilled nursing facility includes providing a call center enabling any of a plurality of health care practitioner terminals to be in audiovisual communication over the network with any of a plurality of patient terminals. The patient is brought into proximity of one of the patient terminals. A connection is established between one of the patient terminals and the call center and the connection is routed to an available health care practitioner at one of the health care practitioner terminals, so that the available health care practitioner may carry on a two-way conversation with a person at one of the patient terminals and visually observe the patient, where the person is the patient, a family member of the patient, and/or a second health care practitioner. The available health care practitioner is permitted to make an assessment of the patient and to conduct an examination of the patient over the network, including by a visual study of the patient.

In accordance with a related embodiment, bringing the patient into proximity of one of the patient terminals may include the person's causing the patient to be in proximity of one of the patient terminals. Bringing the patient into proximity of one of the patient terminals may include the second health care practitioner's having the patient in a position, where the position is standing, sitting or lying down. Establishing a connection between one of the patient terminals and the call center may include the person's placing a call. In accordance with another related embodiment, the method may also include providing medical information of the patient to the available health care practitioner. One of the patient terminals may be portable and capable of wireless communication and bringing the patient into proximity of one of the patient terminals may include moving the one of the patient terminals into proximity of the patient. In accordance with another related embodiment, the method may also include permitting the available health care practitioner to prescribe a treatment. Permitting the available health care practitioner to prescribe a treatment may include referring the patient to a third party, where the third party is a primary care physician, a specialist, a hospital, an emergency room, an ambulance service, and/or a clinic. Referring the patient to a third party may include communicating with the third party via an electronic link included in a relevant segment of a protocol stored in a protocol database resident on a digital storage medium. The available health care practitioner may be a physician, a nurse practitioner or a physician's assistant, and permitting the available health care practitioner to prescribe a treatment may include communicating a prescription over the network to a pharmacy. Communicating the prescription over the network to the pharmacy may include communicating to the pharmacy instructions to be given to the patient pertaining to the treatment of the patient. Permitting the available health care practitioner to prescribe a treatment may include prescribing a treatment order, where the treatment order is an inhalation therapy order, an oxygen order, a laboratory order, a radiology order, a consultation order, an orthopedic hardware order, a diet order, an intravenous fluid order, an activity order, a vital sign order, an intake order, an output order, a diagnostic test order, a rehabilitation order, and/or a supportive therapy order.

BRIEF DESCRIPTION OF THE DRAWINGS

The foregoing features of the invention will be more readily understood by reference to the following detailed description, taken with reference to the accompanying drawings, in which.

DETAILED DESCRIPTION OF THE SPECIFIC EMBODIMENTS

Definitions. As used in this description and the accompanying claims, the following terms shall have the meanings indicated, unless the context otherwise requires:

"Acute," "episodic," and "non-urgent" are terms of art as used in the practice of medicine.

Emergency room overcrowding is partially due to the large volume of non-urgent care being provided by the emergency departments. Patients often access emergency rooms seeking care for conditions that clearly can be managed in other, less intensive settings. Some of these patients simply cannot get access to their own physicians, especially elderly patients in nursing home, assisted living, or other skilled nursing facility environments. Patients who try to access their private physician (sometimes referred to herein as "practicing physician") for minor episodic illnesses often find that they cannot be scheduled for an appointment expeditiously or at a convenient time. Walk in clinics are not always located close by, and while the waiting time to be seen by a physician at a clinic may be less than in an emergency room, such a visit may demand two or more hours. Given the work schedule demands of today's consumer, private physician appointments, emergency department visits, and clinic visits do not provide for the optimal care of patients, especially elderly patients, with acute non-urgent illnesses and some urgent illnesses. Additionally, a bill for treatment of a minor complaint can easily exceed three hundred dollars, which may not cover the true cost of providing the medical care in a hospital setting. Managed care co-payments for these visits are sizable (e.g., fifty to seventy-five dollars) and, not infrequently, the insurer will refuse to pay for the visit in retrospect because the medical problem was minor.

Embodiments of the present invention allow for the remote triage of patients to appropriate settings, and at the same time, allows for comprehensive treatment of acute non-urgent cases and some urgent cases as well as stabilizing treatment of emergent or emergency conditions prior to transfer to an acute care facility or hospital. It should be noted that emergency physicians are best suited to perform the triage function of "sorting" patients into categories of emergent, urgent, and non-urgent conditions because they are specifically trained to manage and care for the full spectrum of conditions that cross all medical and surgical specialties. However, internists and family practitioners are also physicians capable of performing the triage function. Similarly, nurses and nurse practitioners, and physician assistants may also be capable of performing the triage function.

Figure 1:
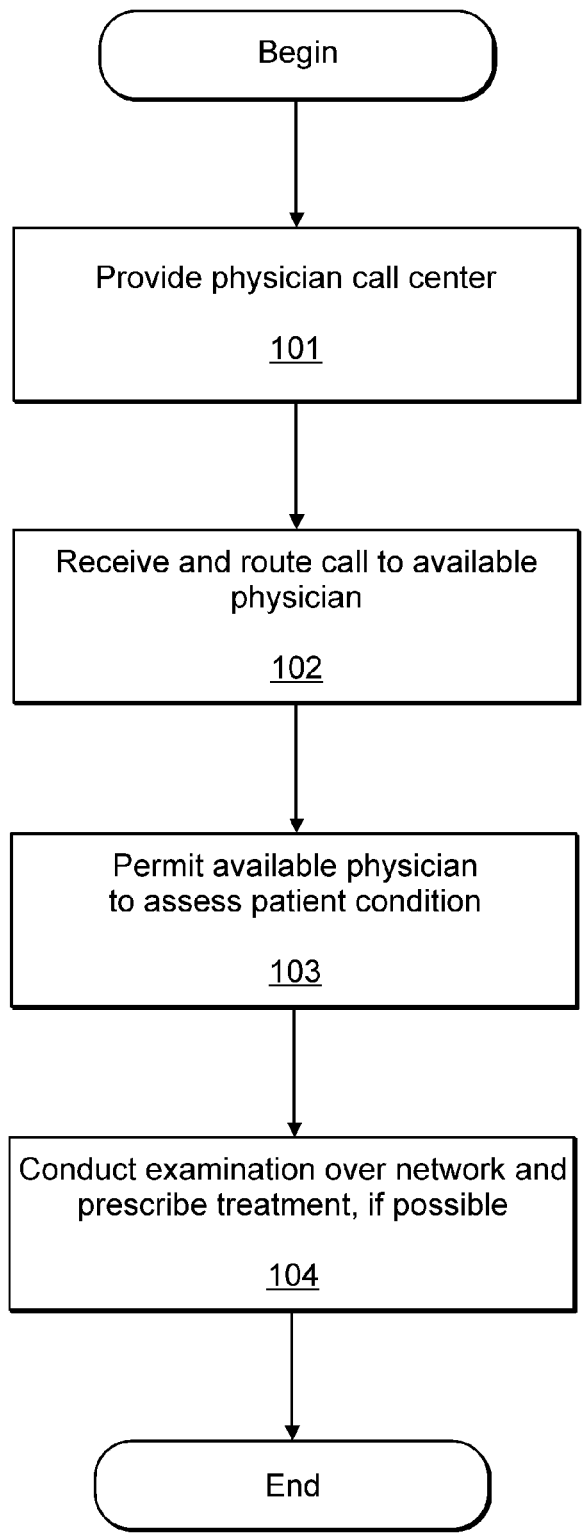
FIG. 1 is a flow chart illustrating a method for delivering medical examination, diagnosis, and treatment services in accordance with an embodiment of the invention.

FIG. 1 is a flow chart illustrating a method for delivering medical examination, diagnosis, and treatment services in accordance with an embodiment of the invention. In process 101, a call center, in accordance with this embodiment, a physician call center, is provided. The physician call center provides integrated services digital network (ISDN) connections to a plurality of physician terminals and a plurality of patient terminals. ISDN is a telephone communication standard for sending voice and digital data over digital telephone lines or normal telephone wires. Although the embodiment of FIG. 1 utilizes an ISDN, any suitable network may be employed, including the Internet, a dedicated Local Area Network (LAN), System Area Network (SAN), Wide Area Network (WAN), or other facility. Connection to the network may be via a modem or other interface device, such as a communications adapter connected to a network over a communication medium. The medium may be either a tangible medium (e.g., optical or analog communications lines) or a medium implemented with wireless techniques (e.g., microwave, infrared or other transmission techniques).

The physician call center may be a single call center that provides international, national or regional connections, or it may be one of a plurality of physician call centers that are in communication with one another to provide such connections. A call from a patient is received at the physician call center in process 102, and the call is routed to an available physician or other health care practitioner. In one embodiment, the available physician must be a board certified physician who is licensed to practice medicine in the state wherein the patient is located. For example, if the patient is calling into the call center from Massachusetts, then the call center will route the patient's call to a physician terminal manned by a board certified physician who is licensed to practice medicine in Massachusetts. In accordance with another embodiment of the invention, the physicians' credentials, including licenses, may be displayed to the patient via a display device.

In process 103, the available physician (or other health care practitioner) is permitted to evaluate the patient's immediate complaint or reason for visit in order to make an assessment of the patient's condition, e.g., may be suffering from an acute non-urgent, urgent or other condition. If a treatable condition is present, an examination may be conducted and treatment may be prescribed in process 104. The examination is conducted via audio video equipment, such as video conferencing equipment, that allows the available physician to interact with the patient in real time in a confidential manner. The examination may include the assessment of the skin (including color and texture), nail beds, eyes and oropharynx of the patient via a video camera and a halogen fiber optic light source. Examples of acute non-urgent conditions include, but are not limited to, acne vulgaris, allergic rhinitis, aphthous ulcer, back pain, bronchitis, minor burns, cellulitis, constipation, contact dermatitis/rhus dermatitis, dental caries or infection, gout or pseudogout, herpes simplex (oral), herpes zoster, hordeolum or chalazion, insect bites or stings, known STD exposure (gonorrhea or chlamydia), Lyme disease (stage I, localized infection), otitis externa, acute otitis media, pharyngitis, scabies, sinusitis, smoking cessation, tendinitis or strain, temporomandibular joint dysfunction syndrome, urinary tract infection (female, uncomplicated) and urticaria. Examples of some acute urgent conditions which may be treatable include, but are not limited to, dehydration, recurrent or chronic congestive heart failure, angina, pneumonia, urinary tract infection (complicated), hypertension, asthma, chronic obstructive pulmonary disease, deep venous thrombosis, diverticulitis, osteomyelitis, cellulitis, pelvic inflammatory disease, pain management, wound care, peptic ulcer disease, hepatic encephalopathy, alcohol withdrawal, transient ischemic attack, seizure disorder, renal failure, bone fracture care, headache, chest pain, shortness of breath, abdominal pain, patient fall evaluation, restraint evaluation, and neuropsychological evaluation. The examination may be conducted in accordance with a protocol, such as discussed below.

Treatment may include home remedies and pharmaceutical remedies that may be prescribed immediately following the examination. Treatment may also include treatment orders such as, but not limited to, inhalation therapy orders, oxygen orders, laboratory orders, radiology orders (e.g., X-Ray, CT scan, ultrasound, MRI), consultation orders, orthopedic hardware orders, diet orders, intravenous fluid orders, activity orders, vital sign orders, intake and output orders, other diagnostic test orders, other rehabilitation orders, other supportive therapy orders, etc. If the patient is suffering from an acute non-urgent condition or some acute urgent conditions, treatment may be prescribed, however the patient may be referred elsewhere as will be described with respect to FIGS. 5A and 5B below.

Comprehensive treatment in circumstances where the patient is determined to be suffering from an acute non-urgent, other non-urgent, or some acute urgent condition is because the examination and treatment of the emergent patient may be limited by the fact that the examination is being conducted remotely, over a network. The inventor has found that assessment and treatment of non-urgent and some urgent conditions are possible under these circumstances. Conversely, more serious illnesses, for example, an acute myocardial infarction, a new stroke, acute appendicitis, etc., are referred to suitable facilities for treatment, such as hospitals with emergency rooms in accordance with an embodiment of the present invention. While an embodiment of the present invention refers or transfers patients with emergent or emergency conditions, it specifically does not preclude stabilizing treatment for such patients prior to referral, transfer, or Emergency Medical Services (EMS) 911 notification.

In addition, the diagnosis of a non-urgent condition may be conducted without a human or mechanical presenter at the patient terminal. However, a human presenter, such as a nurse or other health care practitioner, may be utilized for comprehensive treatment of a non-urgent condition and some urgent conditions in some circumstances, in addition to stabilizing treatment of emergent or emergency conditions as described in more detail below. In an embodiment of the present invention, the examination is conducted by utilizing a video camera and examination light on a patient who is in visual communication with the patient terminal. The patient may be standing, sitting or lying down. In one embodiment there is no need for additional medical instrumentality such as blood pressure readers, thermometers, electrocardiograms, pulse oximeters, peripheral cameras, spirometer, ultrasound or the like, as some diagnosis may be accomplished by observing the patient's physical appearance and by orally obtaining a current history of the patient's illness. In another embodiment, additional medical instrumentality may be used for the diagnosis. In this context, it has proved to be useful to provide wireless connection of an audio-visual terminal with the network, so that the patient terminal may be moved into proximity with the patient, who may, for example, be bed-ridden.

Figure 2:
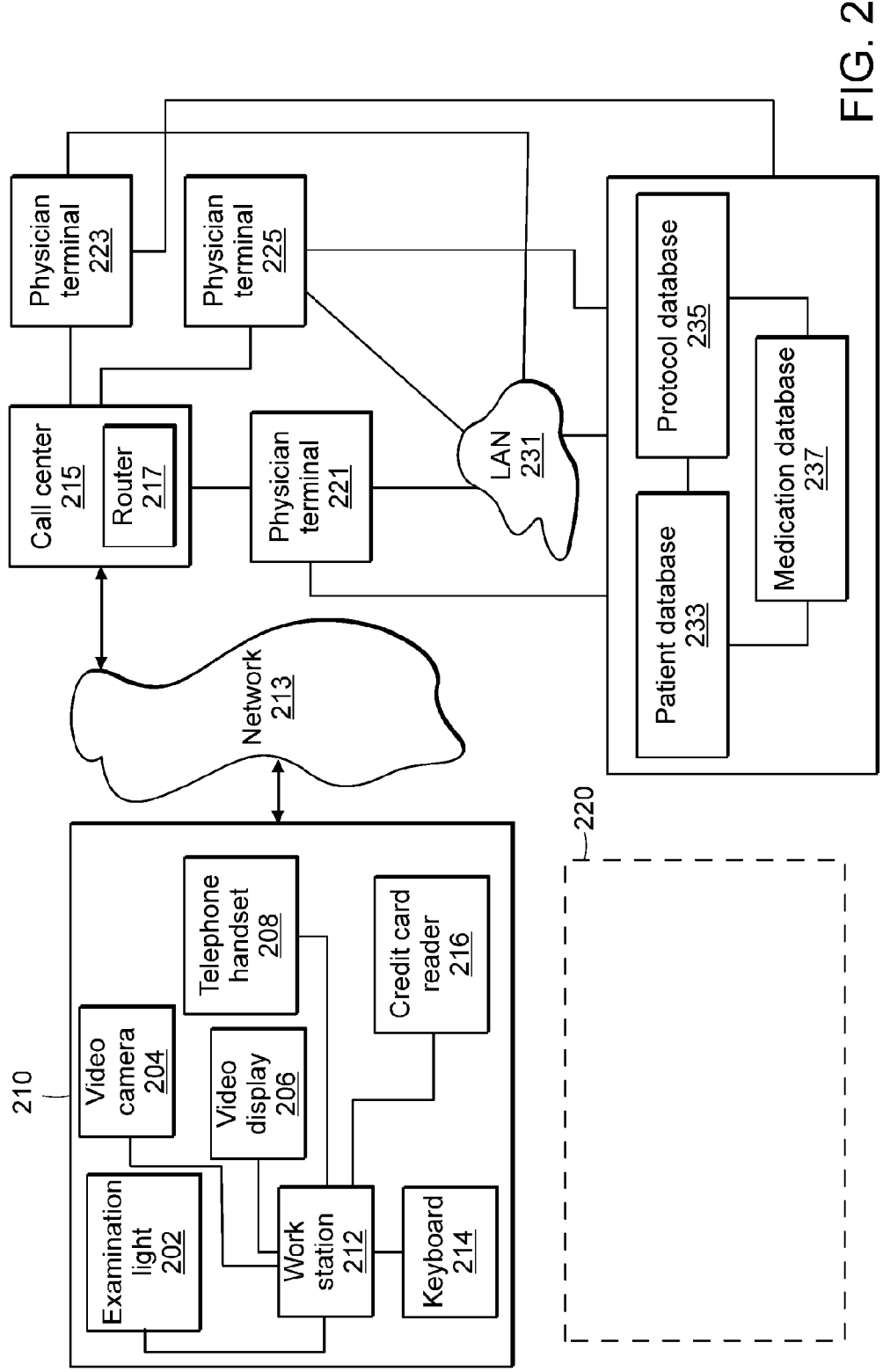
FIG. 2 is a block diagram illustrating a system for delivering medical examination, diagnosis, and treatment services in accordance with another embodiment of the invention.

FIG. 2 is a block diagram illustrating a system for delivering medical examination, diagnosis, and treatment services in accordance with another embodiment of the invention. The system includes a plurality of physician (or other health care practitioner) terminals 221, 223, and 225 in communication with a plurality of patient terminals 210 and 220 via a call center 215 and a network 213. As noted above, the network may be an ISDN network, or the network may be any other network capable of providing audio and video connections. The physician call center 215 includes one or more routers 217 for routing patient calls to an appropriate and available physician terminal 221, 223, or 225.

Each physician terminal 221, 223, and 225 may also be in communication with a protocol database 235, patient database 233, or medication database 237, either locally or via one or more of the networks mentioned above (such as local area network (LAN) 231) and each database may be in communication with another database. When communication is over a network, typically the databases may be accessed via a server on the network. Further, each physician terminal may be in communication with one or more pharmacies, clinics, hospitals, emergency rooms, ambulance services, primary care physician facilities, or specialist facilities.

Each protocol database may include a protocol that guides a physician in conducting a patient evaluation and assessment. The protocol provides a series of segments pertinent to examination, diagnosis and treatment of a patient. For example, in the case of allergic rhinitis, the segment might be displayed to the physician via a display device 304 (see FIG. 4) as shown in Table 1.

TABLE 1

ALLERGIC RHINITIS
(Clinical Programs and Guidelines)

| | |
|---|---|
| PRESENTING COMPLAINT: | Paroxysmal sneezing/nasal congestion |
| AGE RANGE: | 6-65 years |
| MEDICAL HISTORY: | Current medications (BCP?) |
| | Past/Present medical problems? |
| | Allergies |
| | LMP/Pregnancy? |
| | Previous treatment for same? |
| | Social history: drugs, alcohol, smoking |
| PREDISPOSING FACTORS: | Allergies to foods or medications |
| | Environmental allergies: animal fur, plants, dust, molds etc. |
| SYMPTOMS: | Paroxysmal sneezing (especially in a.m.) |
| | Nasal congestion/clear rhinorrhea |
| | Post-nasal drip |
| | Tearing, itchy eyes |
| | Cough |
| SIGNS: | Allergic shiners |
| | Allergic salute |
| | Turbinate edema |
| | Conjunctival injection |
| | Clear nasal discharge |
| WARNING SIGNS: | Fever >101° F./tachycardia |
| | SOB, wheezing* |
| | Difficulty swallowing* |
| | * To Emergency Dept. immediately |
| DIFFERENTIAL DIAGNOSIS: | Sinusitis |
| | Nasal polyps |
| | Cocaine use |
| | Deviated septum |
| TREATMENT: | Usual course several weeks to several months |
| | Primary: Nasal Steroids |
| | beclomethasone (e.g., Beconase): 1-2 sprays/nostril bid |
| | fluticasone (e.g., Flonase): 2 sprays/nostril qd |
| | budesonide (e.g., Rhinocort): 2-4 sprays/nostril qd |
| | Alternative/Adjunctive: |
| | Antihistamines: |
| | loratadine (e.g., Claritin): 10 mg po qd (syrup 5 mg/5 ml) |
| | cetirizine (e.g., Zyrtec): 10 mg po qd (syrup 5 mg/5 ml) |
| | fexofenadine (e.g., Allegra): 60 mg po bid |
| | dimetapp (OTC) |
| | tavist (OTC) |
| | Mast-cell stabilizers: |
| | cromolyn sodium (e.g., Nasalcrom): 1 spray/nostril qid |
| OTHER CONSIDERATIONS: | Side effects of intranasal steroids include irritation and rarely nasal ulceration |
| | Nasal steroids may take a few days to show response |
| | May not need nasal steroids for mild disease |
| | Immunotherapy best reserved for severe cases and for patients who are symptomatic for more than 6 months |
| DISCHARGE INSTRUCTIONS: | To Emergency Department/Primary Care Physician if no improvement in 2-3 days. Give patient discharge instructions. |

ASK IF ANY QUESTIONS OR COMMENTS

Hyperlink text or other automated or electronic communication devices may be provided within the protocol to facilitate the transfer of information from the physician terminal to one or more third parties. A third party may include a primary care physician, a specialist, a hospital, an emergency room, an ambulance service, a clinic, a pharmacy or any combination thereof. For example, if the physician detects one of the warning signs that indicate that immediate emergency care is necessary, he or she may select, e.g., click or double click on, the warning sign, and communication may automatically be established between the physician and an ambulance service or emergency room. Similarly, if the physician deems that a prescription drug is appropriate for the treatment of the patient, the physician may select, e.g., click or double click on, the appropriate prescription, such as one of the nasal steroids listed above, and the prescription will be forwarded to the pharmacy of the patient's choice along with instructions for use of the steroid.

More generally, the protocol may involve, among other things, obtaining from the patient or another health care practitioner, such as a nurse, a history of the current illness or immediate complaint. An example of a general protocol for assessment of a patient is provided in Table 2 below.

TABLE 2

(General Protocol)
TREATMENT OF EXISTING CONDITION

| | |
|---|---|
| PRESENTING COMPLAINT: | Need drug prescription and/or medical advice. |
| AGE RANGE: | Greater than 5 years. |
| MEDICAL HISTORY: | Current medication (BCP?) |
| | Past/Present medical problems |
| | Allergies |
| | LMP/Pregnancy |
| | Previous treatment for same current illness? |
| | Social history: drugs, alcohol, smoking |
| REASONS FOR SEEKING PRESCRIPTION OR TREAMENT: | Unable to secure timely visit with primary care physician |
| | Medication replacement/refill |
| | On vacation, forgot medications |
| | Just moved, need refill until seen by new Primary care physician |
| | Same condition present which was relieved in past by certain medications |
| SYMPTOMS: | Are the symptoms or medical condition essentially the same as that for which the medication(s) were first prescribed? |
| | Have any new (other) medical problems arisen since the medication(s) (in question) were last prescribed? |
| SIGNS: | Any significant change in vital signs since last prescription filled? |
| | Consider patient's present temperature, pulse, blood pressure and respiratory rate |
| | Any significant change in physical appearance or physical findings since last prescription filled? |
| WARNING SIGNS: | Any significant change in symptoms, vital signs, or physical signs from previously as patient presents to the available physician? |
| TREATMENT: | Specific: |
| | Write R$_x$ for patient if it seems appropriate |
| | General: |
| | Use discretion in prescribing narcotics or sedative/hypnotic medication(s) (may need to check old records) |
| | If prescribing narcotics, do not exceed 3-5 day supply |
| | Use discretion in prescribing medication(s) for more serious conditions (e.g., cardiac, diabetic medication(s), etc.) and only prescribe enough to last until patient get to primary care physician/emergency department |
| DISCHARGE INSTRUCTIONS: | To emergency department/primary care physician if any significant change in symptoms or physical findings occur while patient is on medication(s) |

ASK IF PATIENT HAS ANY QUESTIONS OR COMMENTS

The general protocol, as outlined above, involves obtaining from the patient, the patient's family or another health care practitioner: a history of the patient's present or immediate illness; a past medical history, including current medications and allergies; a review of systems; and a social history. The protocol further involves: conducting a physical examination on the patient (including by visual inspection); developing a differential diagnosis (e.g., a list of possible and/or probable diagnoses based on the history and physical examination); assessment for mitigating factors that may result in a change in treatment or referral to an alternative setting for treatment; treatment, which may consist of advice only or may result in the electronic transmission of one or more prescriptions to a pharmacy of the patient's choice; review of other considerations so as to tailor the patient's treatment based on the patient's condition, co-morbidities (e.g., diabetes mellitus), allergies, current medications and known side effects, and drug interactions; and a review of the diagnosis, treatment, and aftercare instructions with the patient, including disposition (e.g., referral for follow-up evaluation as well as transmittal of a synopsis of the present visit, with the patient's permission, to his or her private practitioner.)

When appropriate from the general protocol, the physician invokes condition specific protocols as necessary. The treatments listed in the condition specific protocols represent common, cost effective treatment for the corresponding conditions. However, in each case there are other acceptable treatments that fall within the standard care and which may be prescribed by the physician when indicated and appropriate based on the patient's condition and mitigating factors. The general protocol also applies to a patient whose condition is not entirely consistent with one of the existing protocols, but who nevertheless is clearly suffering from an acute non-urgent or some urgent condition that is appropriate for comprehensive treatment through this modality.

New condition specific protocols, with the corresponding aftercare instructions, may be added from time to time, and the existing protocols and aftercare instructions may be modified and updated from time to time. In each case, any additions and/or modifications will be synchronized throughout all call centers and physician terminals.

Each physician terminal may be in communication with a patient database 233 via a network such as LAN 231. The patient database may include a record of each patient who has used the system, as well as the diagnosis made and treatments prescribed for each visit. The patient database may also include the patient's name, address, phone number and primary care physician as well as the name of any physician or specialist the patient has contacted via the system. By accessing a patient database, an available physician may obtain information vital to the patient's care and prevent the patient from abusing the system, e.g., by obtaining multiple and unnecessary prescriptions. The patient database may include specific preferences for care (e.g., Orthopedic Physician "Smith" prefers a specific type of non-occlusive dressing for his patients) as ordered, or recommended by the patient's primary care physician or specialist. Further, the available physician may have an assistant who may access the patient database for information related to a patient's general history or demographics.

The protocol, patient, and medication databases associated with the system may be used under suitable program control for purposes including:

1) providing a permanent record of each physician/patient interaction;
2) providing a permanent record of the demographics of all patients who utilized the services of the system;
3) guiding the available physician through the physician/patient interaction by means of:
    a) proprietary protocols, including hyperlinks between medications recommended in the protocols and a medication database;
    b) various menus leading to the final prescription(s), if any, aftercare instructions, receipt and other information (such as work or school notes) provided to the patient;
    c) various advisories and warnings triggered by the choice of a specific medication and/or the patient's condition (such as pregnant, nursing, pediatric age range, etc.);
    d) allowing the physician to prescribe outside the standard protocols, when appropriate, by means of choosing medications directly from the database, and/or changing dosage, frequency and/or amount dispensed for medications chosen through the protocols;
    e) allowing the physician to prescribe as per the orders, preferences, guidelines, care maps, or direction of the patient's primary care physician or specialist
    f) limiting the physician in any manner specified or programmed by the system administrator (e.g., limiting controlled substances to no more than twelve tablets);
    g) automatically adding the physician's name, facsimile signature, DEA number to prescriptions (based on a login or password);
4) allowing all call centers to interact so that:
    a) protocols, aftercare instruction sheets and the medication database are standardized at least every twenty-four hours;
    b) patient records are synchronized and updated frequently (e.g., every five minutes) so that each physician call center will always have a current patient record in the event that a patient utilizes more than one physician call center or patient terminal;
5) providing a Chief Medical Officer with a variety of quality practice/risk management reports on individual call centers, individual physicians and the system as a whole;
6) allowing the system administrator to update protocols, aftercare instructions, work or school notes, the medication database and any other appropriate component of the system;
7) allowing the system administrator to add new protocols, aftercare instructions, work or school notes and other appropriate components and to archive existing components;
8) allowing the system administrator to update the medication database by means of:
    a) modification to existing medications, advisories, warnings and other parameters;
    b) adding new medications, advisories, warnings and other parameters;
    c) archiving existing medications, advisories, warnings and other parameters;
    d) setting or changing limitations on existing or new medications (e.g., limiting amount dispensed);
9) limiting access to the databases to authorized personnel by means of a login, password, key or other device linked to an access level specified by the Chief Medical Officer;

10) limiting access to reports and functions that allow modification of the databases to the system administrator and those specified by the Chief Medical Officer or other executive.

The patient database, under suitable program control, may capture the following information on each patient:
1) demographic data such as name, permanent address, date of birth, phone number, work phone number, primary care physician (name, address, phone number, fax number), name of local hotel or motel, address, and phone number (if the patient is traveling), name of skilled nursing facility or other site of service, name and title (e.g. RN, LPN) of telepresenter at patient site, if any;
2) basic medical information such as reason for visit, general appearance, pregnant, breast feeding, known allergies and reactions;
3) a diagnosis based on the protocol chosen or as entered by the available physician;
4) any medication(s) prescribed by the available physician;
5) any comprehensive treatment(s) ordered by the available physician;
6) any stabilizing treatment(s) ordered by the available physician
7) any work or school note provided by the available physician.

Additionally, one or more of the databases, under suitable program control, may capture the following information on each physician associated with the system:
1) name as it should appear on prescriptions and patient video screens, including degree (e.g., M.D., D.O.);
2) DEA number (which will be printed on prescriptions);
3) facsimile signature (which will be printed on prescriptions);
4) dates and times "logged in" and "logged out";
5) patients evaluated (number and names);
6) diagnoses made;
7) any other information necessary for designated reports.

Further, one or more of the databases, under suitable program control, may provide standard reports to be generated upon authorized demand such as:
1) for each physician call center and for all call centers combined:
   a) total number of calls;
   b) average number of calls per day and per operational hour;
   c) average number of calls per time of day and day of week;
   d) average duration of calls;
   e) number and ratio/percent of new patients versus repeat patients;
2) for each patient terminal and third party entity (e.g., primary care physician, hospital, emergency room, ambulance service, clinic, specialist, and pharmacy):
   a) calls originating from each terminal (total number of calls, average number of calls per day and per operational hour, average number of calls per time of day and day of week);
   b) transmissions to each third party entity (total number of calls, average number of calls per day and per month);
3) for each physician (each item to be compared to system average for all physicians):
   a) total calls and hourly average;
   b) average duration of calls;
   c) total prescriptions written and ratio/percentage of prescriptions to calls;
   d) ratio/percent of "no changes" to total number of calls;
   e) time in and time out (for payroll and to monitor timeliness);
   f) hours worked;
   g) prescriptions for controlled substances or other specified medications (total number and ratio/percent of total prescriptions for that physician);
   h) prescriptions written for medications not in database;
4) for each physician assistant (each item to be compared to system average for all physician assistants):
   a) total calls and hourly average;
   b) average duration of calls;
   c) time in and time out;
   d) hours worked;
5) patient demographics:
   a) number and percent of patients in various age ranges, to be specified;
   b) average age of patients;
   c) sex of patients (total numbers, ratio/percents);
   d) average number of visits/calls per patient;
6) other reports as specified from time to time by the Chief Medical Officer or other system executive.

One or more of the databases, under suitable program control, may also provide the following functions when a physician is logged onto the system and a patient initiates a physician/patient interaction:
1) the physician and/or physician's assistant may be able to:
   a) enter demographic data on a new patient via a keyboard or other input device;
   b) access and update demographic information on an existing patient (one who has utilized the system in the past);
   c) view the demographic information throughout the interaction via a display device;
2) the physician may be able to:
   a) enter medical data on a new patient (e.g., allergies, current medications, pregnancy, breast feeding, etc.) via a keyboard or other input device;
   b) view medical information from prior interactions on existing patients via a display device;
   c) update information that may have changed since the prior visit (e.g., allergies, current medications, pregnancy, etc.);
   d) make no modifications to the prior record of medications prescribed, diagnoses, or similar information;
3) the physician may view any existing protocols while interviewing the patient, and may switch to a different protocol at any time;
4) the physician may choose a medication listed in a protocol, thereby activating a hyperlink (or other communication link) to a medical database or pharmacy thereby creating a prescription for the medication that is forwarded to a pharmacy, either free standing or located within a skilled nursing facility, occupational health setting, or other health care setting;
5) the physician may choose a third party to which the patient should be referred as listed in a protocol thereby activating a hyperlink (or other communication link) to the third party;
6) the physician may choose a work or school note listed in a protocol thereby activating a hyperlink (or other communication link) and generating the note, or the physician may initiate a note directly by entering the note into an input device thereby generating a note that is forwarded to the patient;

7) the physician may choose any medication directly by entering the medication in the medication database via a keyboard or other device, thereby creating a prescription for any chosen medication that is then forwarded to a pharmacy;

8) the physician may bypass the protocol and medication databases and prescribe a medication by entering it directly on a prescription screen via a keyboard or other input device thereby generating a prescription that is forwarded to a pharmacy (this may trigger a "red flag");

9) once a prescription(s) is generated there may be a review function by which the physician may:
   a) delete the prescription for any particular medication;
   b) change the dosage, frequency, amount dispensed or other parameters within any restrictions imposed (e.g., amount is restricted for controlled substances, the physician may prescribe less than the amount designated in the protocol but no more than the specified limit);

10) when a prescription(s) is transmitted to a pharmacy, the corresponding aftercare instruction sheet (based on the chosen protocol) and a receipt may be transmitted to the pharmacy or directly to the patient's location;

11) whenever a medication is chosen by the physician, the following information for that particular medication (contained in the medication database) may automatically be displayed to the physician (even if it does not appear on the prescription itself):
   a) any advisory or warning for that particular medication;
   b) "use in pregnancy" instructions (automatically if the patient information indicates the patient is pregnant);
   c) "use in nursing mothers" instructions (automatically if the patient information indicates that the patient is nursing);
   d) "use in pediatrics" instructions (automatically if the patient's demographic information indicates that he or she is in the pediatric age group); if the information for that medication specifies a particular age range or limitation ("not approved by persons 6 years or younger") a warning will be displayed to the physician if the patient meets the range or limitation;
   e) "use in elderly or geriatrics" instructions (automatically if the patient information indicates that the patient's age is 60 or greater);

12) the physician may electronically indicate that he or she has viewed the medication information outlined in 11) above (e.g., by selecting or clicking on an "OK" icon or field);

13) the database, under suitable program control, may allow simultaneous and serial use of the database by a physician and his or her assistant:
   a) after the physician completes the medical interaction with the patient, an assistant may assume control of the open database, record demographic data if not previously recorded, verify a credit card transaction, and/or transmit a prescription(s), aftercare instruction sheet(s), and/or work or school note chosen by the physician;
   b) the assistant may record demographic information either before or after the physician/patient interaction;

14) the database, under suitable program control, may interact with credit card reader software so that prescription(s), work or school notes and aftercare instruction sheet(s) are not transmitted until payment has been verified by the assistant or physician and the assistant or physician activates the transmittal;

15) the database, under suitable program control, may have the ability to:
   a) place limitations on medications as specified by the system administrator (e.g., controlled substances may be limited to no more than twelve tablets, although fewer than twelve tablets may be prescribed at the physician's discretion);
   b) identify specified medications (by color-coding, a message box or other means) that should be prescribed only when certain conditions are met (e.g., as a replacement for an existing prescription or when the patient has had previous experience with the same medication;

16) the database, under suitable program control, may have the ability to link the medication database to the patient database so that appropriate warnings regarding cross-allergies and/or medication interactions may be generated;

17) the database, under suitable program control, may have the ability to link to a video database in order to generate videos illustrating patient care and prevention techniques, such as generating a video displaying the proper way to lift a heavy object to a patient who is suffering from back pain.

Figure 3:
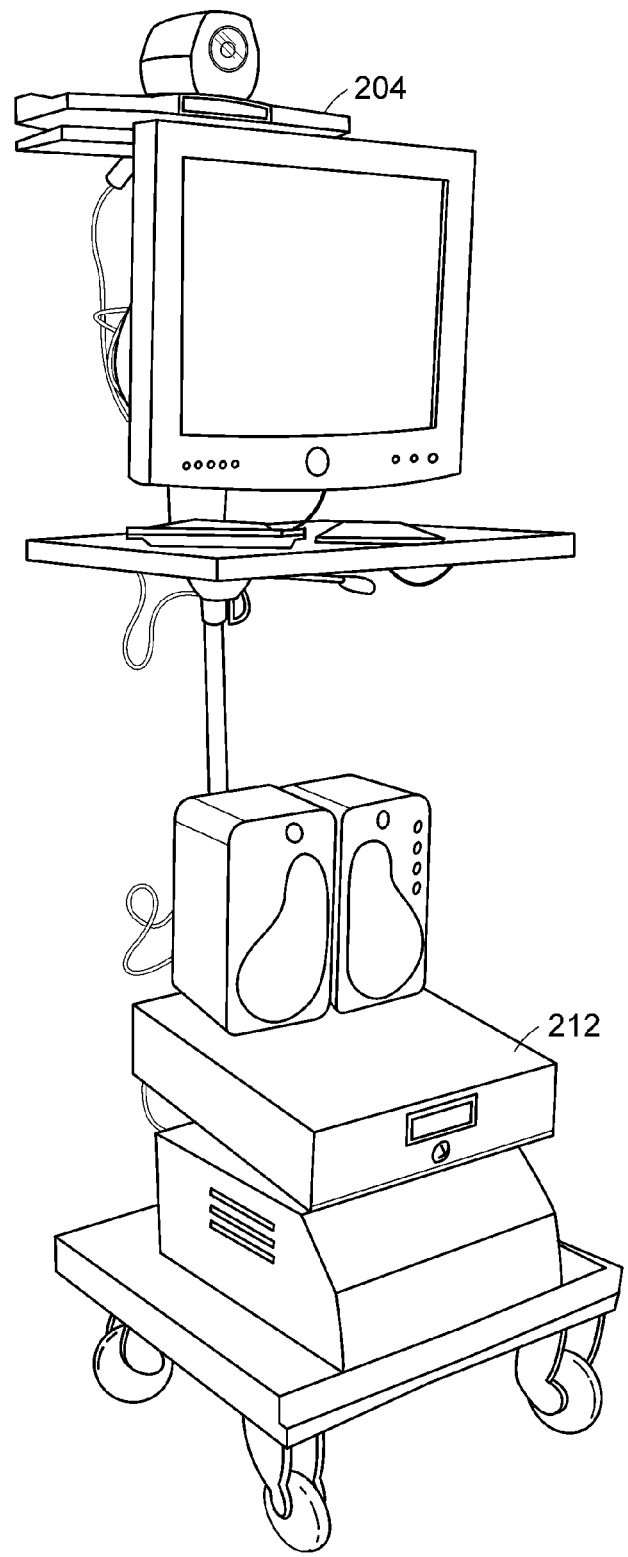
FIG. 3 is an image of a portable patient terminal in accordance with an embodiment of the present invention.

Each patient terminal 210 or 220, which may be a kiosk or a portable unit, such as shown in FIG. 3, includes a work-station 212. A video camera 204, e.g., TANDBERG 880 MXP produced by TANDBERG, New York, N.Y., is in communication with the work-station 212, as is an examination light 202 to provide an available physician with a clear visual view of the patient. The video camera is controlled by the available physician via the work-station in the physician terminal. The video camera enables the available physician to scan the patient vertically (in a "tilt" mode), scan the patient horizontally (in a "pan" mode), and provide the available physician with a detailed and magnified image of any part of the patient's body (in a "zoom" mode). A patient terminal 210 or 220 may also include a video display by which the patient may view the available physician, the available physician's name, written instructions supplied by the available physician, video instructions and the available physician credentials in real time. The patient or another health care practitioner or a family member initiates a call to a physician call center 215 by picking up a telephone handset 208 or otherwise establishing a connection. The patient terminal may also include a credit card reader 216 by which payment for services provided by the available physician may be made. Further, the patient terminal may include a keyboard 214 to allow a technician to configure and update the patient terminal. Patient terminals may be established in skilled nursing facilities, shopping centers, malls, supermarkets, department stores, gas stations, pharmacies, hotels, office complexes or other workplaces.

Figure 4:
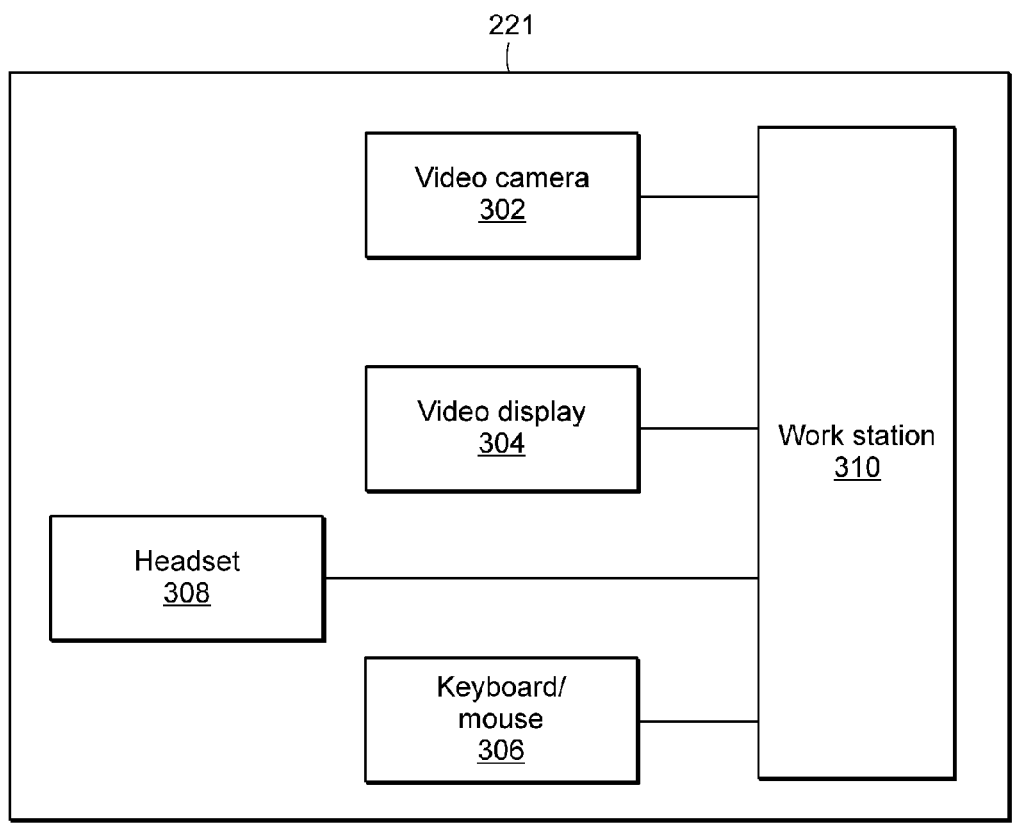
FIG. 4 is a block diagram illustrating a physician or other health care practitioner terminal in accordance with an embodiment of the present invention.

FIG. 4 is a block diagram illustrating a physician (or other health care practitioner) terminal in accordance with an embodiment of the present invention. Each physician terminal 221, 223, or 225 includes a work-station 310 in communication with the physician call center 215 and one or more databases, such as 233, 235, 237 shown in FIG. 2, a video display 304 by which to view the patient, and a headset 308. A physician terminal may also include a video camera 302. The video camera 302 allows a patient, a patient's family or another health care practitioner to view the physician attending the patient. The physician terminal may also include a facsimile device (not shown) by which instructions pertinent to patient care and treatment may be forwarded to a pharmacy along with a prescription in accordance with one embodiment of the invention. Similarly, such instructions may be sent over the network to a pharmacy via the work-station 310 and keyboard and mouse 306. The instructions may also be displayed to the patient, the patient's family or another health care practitioner via video display 206, as shown in FIG. 2. An example of patient care and treatment instructions for allergic rhinitis is shown in Table 3.

TABLE 3

ALLERGIC RHINITIS (Aftercare Instructions)
Allergic rhinitis means congestion of your nose caused by environmental allergies (hay fever) and similar situations.

| | |
|---|---|
| Please follow these instructions carefully: | Take any prescribed medicines as directed. Try to avoid whatever is causing the allergic reaction (such as staying indoors, with air conditioning, during heavy pollen season). Most seasonal allergies can be controlled with medication and get better when you are no longer exposed to whatever is causing the allergic reaction (such as when the pollen count decreases). However, if you become worse in any way, get checked by your doctor, go to an Emergency Department or see an allergy specialist. |
| Go to an Emergency Department or see your own doctor right away if any danger signs develop, including the following: | Swelling of your face, tongue or neck. Pain or pressure over your sinuses (forehead or cheeks). Fever (over 102° F.), sweats or shaking chills. Trouble breathing or swallowing. Wheezing or hoarse voice. New or worsening rash (hives). Dizziness, fainting or feeling "flushed." Chest pain or chest discomfort, including tightness. Anything else that worries you. |

Emergency Departments are open 24 hours a day for any problems.

Figure 5A:
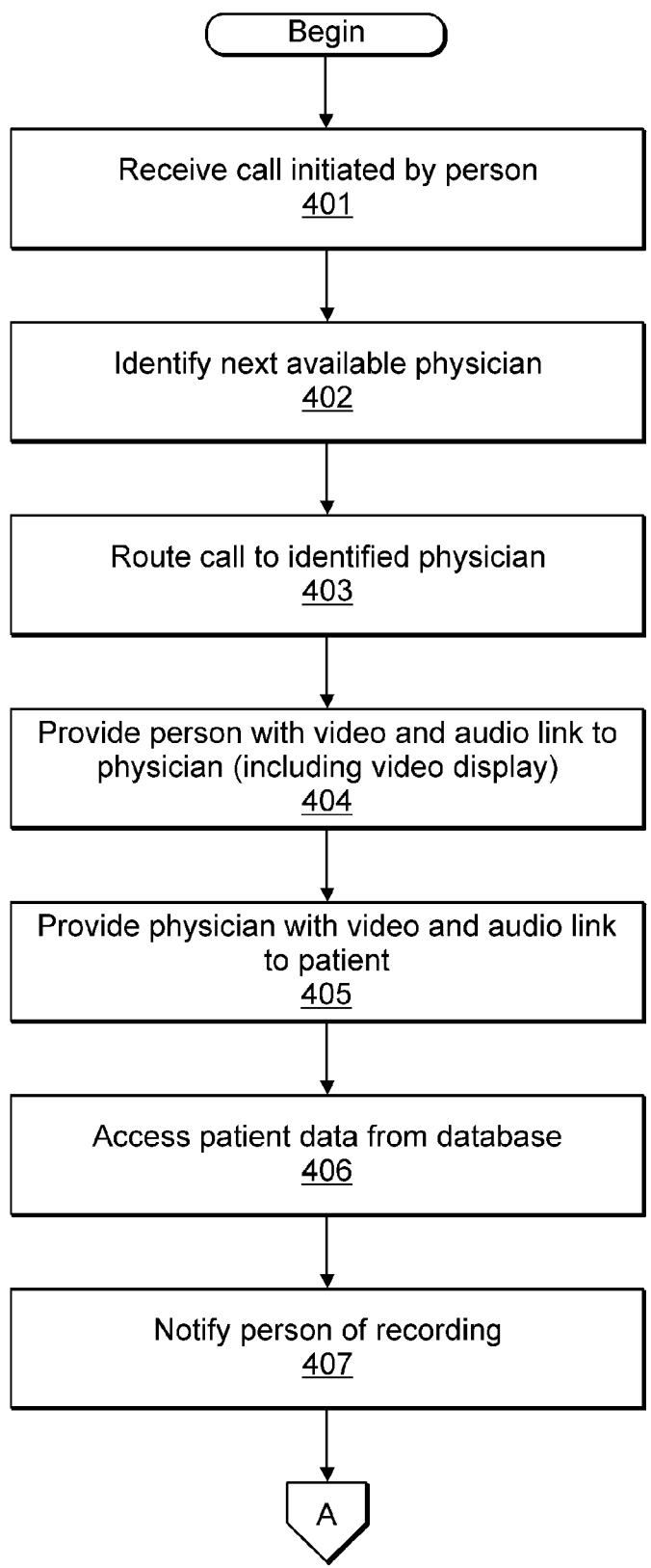
FIGS. 5A and 5B are a flow chart illustrating a method for delivering medical examination, diagnosis and treatment services in accordance with another embodiment of the invention.
Figure 5B:
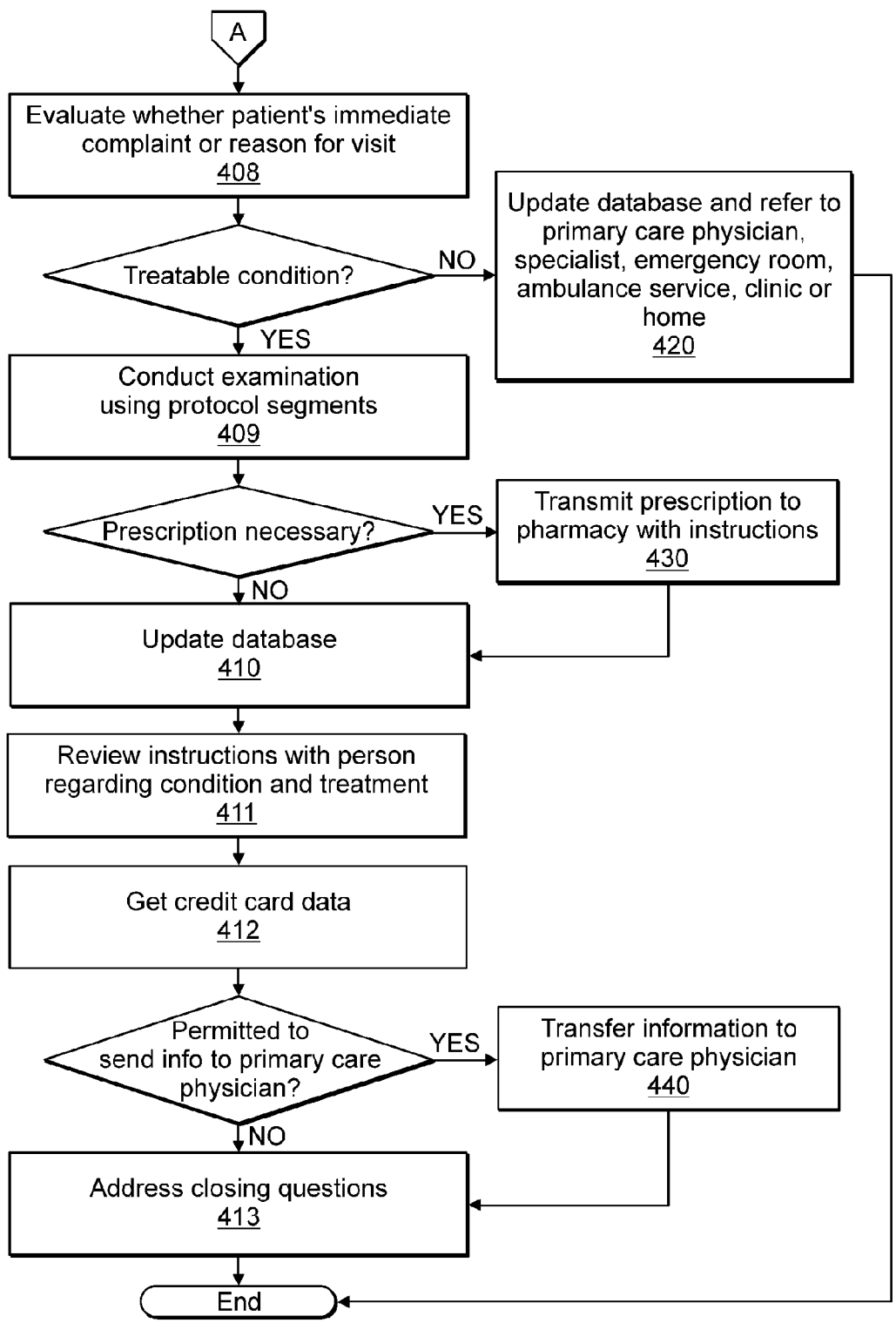

FIGS. 5A and 5B are a flow chart illustrating a method for delivering medical examination, diagnosis and treatment services in accordance with another embodiment of the present invention. In process 401, a call is initiated by a person, such as the patient, the patient's family or another health care practitioner, and is received at the physician call center 215. The next available physician is identified 402 and the call is routed to the identified available physician at a physician terminal (such as 221, 223, or 225) in process 403. When the patient, patient's family or another health care practitioner calls the physician call center and an available physician has been identified, the patient, patient's family or another health care practitioner is provided with a video and audio link, which may include a video display 206, to the physician in process 404. Similarly, the physician is provided with a video and audio link to the patient in process 405. Any patient information that may be stored in the patient database 233 is accessed by the available physician in process 406. Such information is accessed to provide the available physician with a history of the patient, any conditions or illness the patient has been treated for, and any medications that the patient has been prescribed.

In process 407, the patient, patient's family or another health care practitioner is notified that the visit may be recorded. Recording the visit provides information for the patient database and insures the integrity of the care that the patient receives. An evaluation of the patient's immediate complaint or reason for the current visit is performed by the physician in order to make an assessment as to what condition the patient may be suffering from, e.g., an acute non-urgent, other non-urgent, or urgent condition in process 408. If the patient is suffering from such a non-treatable condition, the patient database 233 will be updated and the patient will be referred to a primary care physician, specialist, emergency room, ambulance service, clinic, or home in process 420. As discussed above, this can be accomplished through hyperlink connections (or other electronic connections) available to the physician via the system.

If the available physician determines that the patient may be suffering from a treatable condition, an examination is conducted 409, e.g., using the protocol segments accessed from the protocol database 235. The protocol segments may provide the physician with advisory or warning messages as discussed above. The available physician (or other health care practitioner authorized to do so, such as a nurse practitioner or a physician's assistant) may assess whether a prescription is necessary to treat the condition. If a prescription is necessary, the available physician (or other health care practitioner) may transmit the prescription to the patient, the patient's family, another health care practitioner or to a pharmacy, along with instructions for proper use of the prescription, aftercare instructions, and any necessary notes as described above, via hyperlinks or other electronic connections (process 430). Following transmittal of the prescription and instructions to the pharmacy, the patient database will be updated, in process 410, with a record of the visit, including diagnosis and treatment. If no prescription is necessary, the patient database will simply be updated 410 with a record of the visit and diagnosis.

In process 411, instructions pertinent to the patient's condition and treatment are reviewed with the patient, patient's family or another health care practitioner and these instructions may be displayed to the patient, patient's family or another health care practitioner via the video display 206, as shown in FIG. 2. As noted above, video demonstrations related to the patient's care and treatment may be displayed to the patient, patient's family or another health care practitioner as necessary. Credit card or insurance information may be obtained from the person in process 412, either by the physician or an assistant. The patient, the patient's family or another health care practitioner is asked if he or she would like information regarding the visit to be sent to the patient's primary care physician and if he or she so desires, the information is transferred, via hypertext link or other electronic connections, in process 440, to the primary care physician. Any closing questions, comments and/or concerns of the patient, patient's family or another health care practitioner are addressed in process 413 and the visit is ended.

Figure 6:
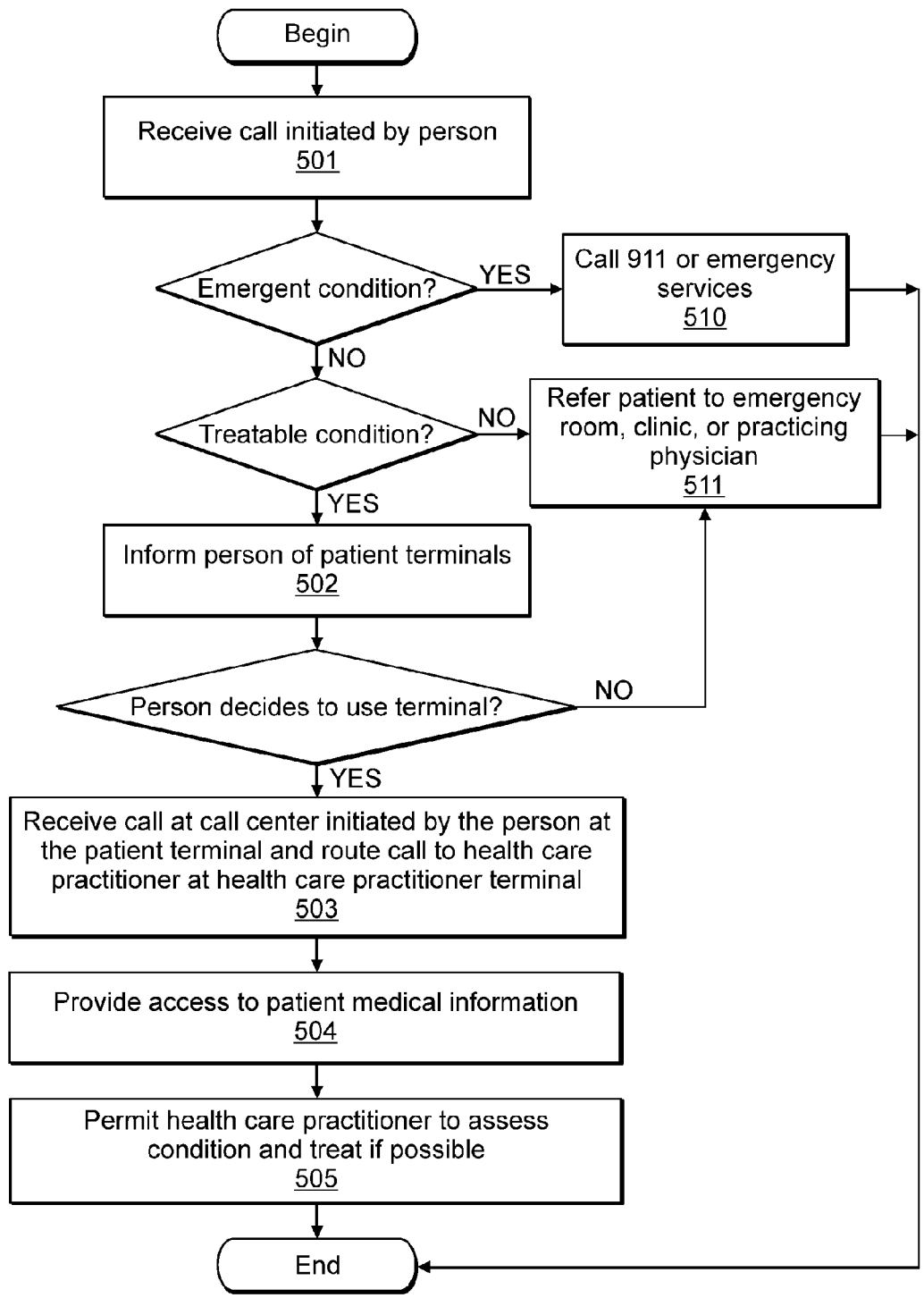
FIG. 6 is a flow chart illustrating a method for providing a covering physician service in accordance with an embodiment of the present invention.

FIG. 6 is a flow chart illustrating an embodiment wherein the systems and methods described with respect to FIGS. 1-5B may be used to provide a covering physician service via a network. Such a covering physician service may be offered by, for example, a physician, a health care management system (such as a healthcare management organization ("HMO"), a preferred provider organization ("PPO") or a point of service plan system ("POS")), a health insurance provider, a hospital, a clinic, a nursing home or skilled nursing facility or other health care facilities. Such a covering physician service may be provided by a physician or other health care practitioners as may be authorized or allowed by law.

In accordance with the method illustrated in FIG. 6, if the patient is unable to access his or her primary care physician (or another practicing physician providing care to the patient) a call may be initiated by a person, such as the patient, patient's family or another health care practitioner, and is received in process 501 by an answering service associated with the practicing physician. The answering service determines, via information provided by the person, whether the patient is exhibiting symptoms of an emergent condition, and if so, the answering service contacts 911 emergency service or some other emergency service in process 510. If it is determined that the patient in not exhibiting symptoms of an emergent condition, the answering service may then determine, via information provided by the person, if the patient is exhibiting symptoms of a treatable condition. If the patient is exhibiting symptoms of a treatable condition, the answering service will inform the person, in process 502, that he or she may use the patient terminals for immediate treatment of the condition. The person may then decide to use a patient terminal, wait to talk to or to see the practicing physician, or go to an emergency room or a clinic. If the answering service determines that the patient is exhibiting symptoms that are not related to a treatable condition, the answering service may refer the patient, in process 511, to an emergency room, a clinic, or to the practicing physician (when the practicing physician is available) for treatment.

If the person decides to use one of the patient terminals, then, in process 503, a call initiated by the person at one of the patient terminals will be received by a call center. The call center enables any of a plurality of physician or health care practitioner terminals to be in audio-visual communication over the network with any of a plurality of patient terminals and the call center will route the call to a physician or other health care practitioner at a physician or health care practitioner terminal. As described in connection with the physician call center of FIG. 1, the call center provides communication connections, e.g., ISDN, Internet, LAN, SAN, WAN or other digital facility to a plurality of physician or health care practitioner terminals and a plurality of patient terminals. Here again, the call center may be a single call center that provides international, national or regional connections, or it may be one of a plurality of call centers that are in communication with one another to provide such connections. In process 504, information related to the patient (such as an electronic medical record) may be received at the physician or health care practitioner terminal via the network. The information may be forwarded via a computer or database in the practicing physician's office or by a computer or database associated with the practicing physician, a health care management system or other health care facility or an insurance provider. The physician or health care practitioner may then assess the patient, treat the patient accordingly, and forward updated information related to the patient (such as examination, treatment and prescription details related to the patient's visit to the patient terminal) to the practicing physician via the network in process 505, such as in a manner described with respect to FIGS. 1-5B above.

Figure 7:
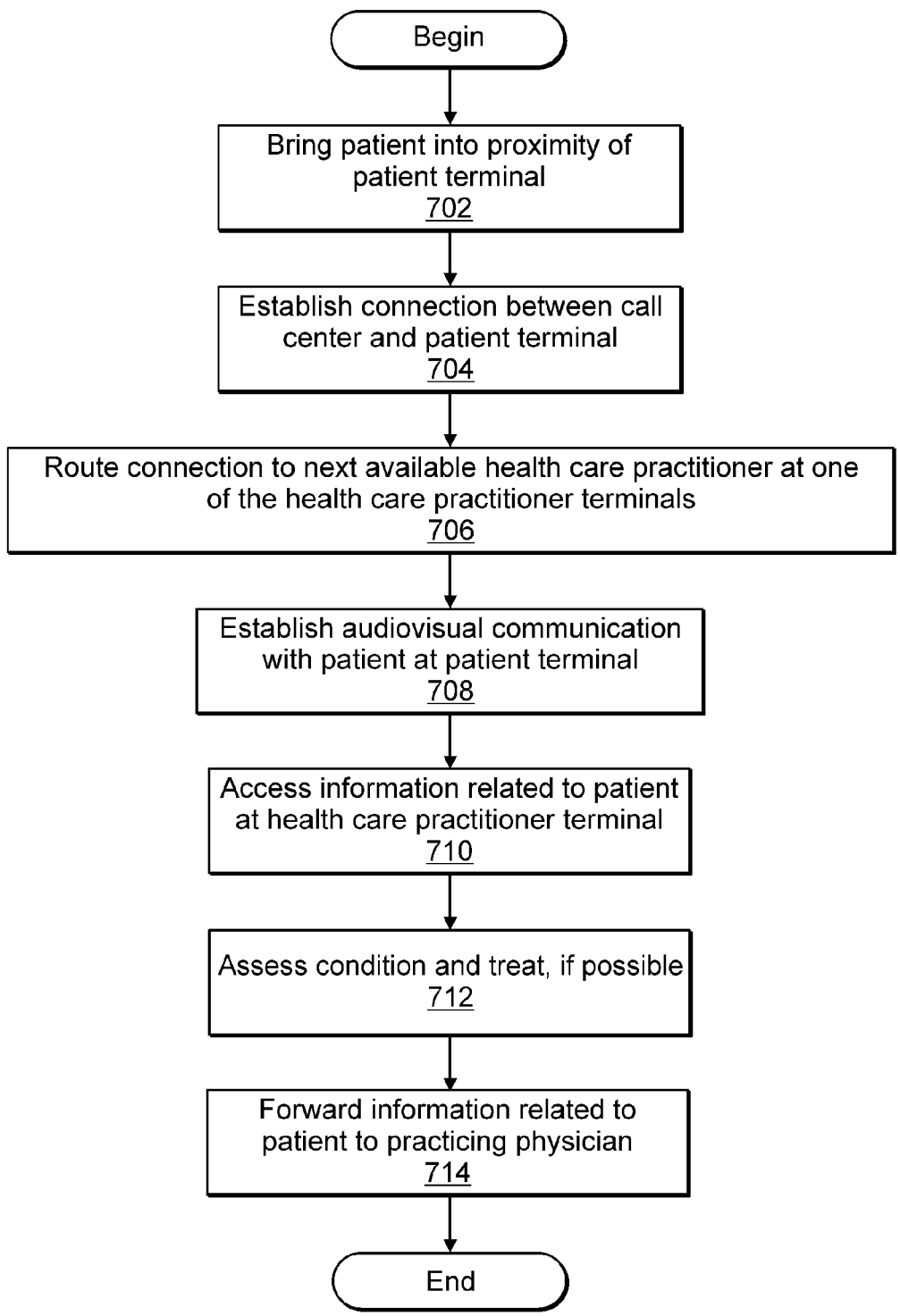
FIG. 7 is a flow chart illustrating a method for delivering medical examination, diagnosis and treatment services in accordance with an embodiment of the present invention.

FIG. 7 is flow chart illustrating a method for delivering medical examination, diagnosis and treatment services in accordance with an embodiment of the present invention. In process 702, a patient is brought into proximity of one of the patient terminals. For example, a portable patient terminal may be moved into proximity of a patient, such as a patient in a skilled nursing facility, by a nurse or nurse's aide, or the patient may be moved into proximity of the patient terminal, e.g., via a wheelchair or other device for transporting the patient. A connection is established between the call center and the patient terminal in process 704. For example, a connection may be initiated by the patient, a member of the patient's family or another health care practitioner, such as a nurse. The connection from the patient terminal to the call center is then routed to the next available physician or health care practitioner at one of the health care practitioner terminals, in process 706. When the connection is routed to the next available health care practitioner, audiovisual communication is established with the patient at the patient terminal so that the physician or health care practitioner is provided with a video and audio link to the patient in process 708. The patient may also be provided with a video and audio link, which may include a video display to the physician or health care practitioner. Any patient information that may be stored in the patient database may be accessed by the available physician or health care practitioner in process 710. Such information may be accessed to provide the available physician or health care practitioner with a history of the patient, any conditions or illness the patient has been treated for, any specific or general instructions or orders from the patients primary care physician or specialist and/or any medications that the patient has been prescribed.

In process 712, an evaluation of the patient's immediate complaint or reason for the current visit is performed by the physician or health care practitioner in order to make an assessment of the patient's condition, e.g., may be suffering from an acute non-urgent, other non-urgent, urgent or emergent condition. If the patient is suffering from an emergent or emergency condition such as described in FIG. 6, Emergency Medical Services or 911 is contacted as in process 510. If the patient is suffering from a non-treatable condition, the patient database 233 may be updated and the patient may be referred to a primary care physician, specialist, emergency room, ambulance service, clinic, or home. As discussed previously, this may be accomplished through hyperlink connections (or other electronic connections) available to the physician or health care practitioner via the system. If the available physician or health care practitioner determines that the patient may be suffering from a treatable condition, an examination is conducted, e.g., using protocol segments accessed from a protocol database 235. The protocol segments may provide the physician or health care practitioner with advisory or warning messages as discussed above. The available physician or health care practitioner may provide definitive comprehensive treatment orders for treatable conditions including non-urgent and some urgent conditions as in process 712. If the available physician or health care practitioner determines that the patient may be suffering from an emergent or emergency condition, then stabilizing treatment orders may be provided while simultaneously contacting Emergency Medical Services through 911. The available physician or other health care practitioner authorized to do so, such as a nurse practitioner or a physician's assistant, may also assess whether a prescription or medication order is necessary to treat the condition. If a prescription or medication order is necessary, the available physician or health care practitioner may transmit the prescription or medication order to the patient, the patient's family, another health care practitioner, such as the patient's nurse, or to a pharmacy, along with instructions for proper use of the prescription or medication order, aftercare instructions, and any necessary notes as described above, via hyperlinks or other electronic connections. Alternatively, if a prescription or medication order is necessary, the available physician may provide a verbal order, e.g., to a nurse participating in the patient's care, who may or may not be present during the videoconference. This shall not obviate the need for later written transmittal of the prescription or medication order and instructions to the pharmacy. Following transmittal of the prescription and instructions to the pharmacy, the patient database is updated with a record of the visit, including diagnosis and treatment. If no prescription is necessary, the patient database may simply be updated with a record of the visit, diagnosis, and any other orders or actions taken.

Instructions pertinent to the patient's condition and treatment may be reviewed with and/or displayed to the patient, the patient's family or another health care practitioner via a video display 206, such as shown in FIG. 2. As noted above, video demonstrations related to the patient's care and treatment may be displayed to the patient, patient's family or another health care practitioner as necessary. The patient, the patient's family or another health care practitioner may be asked if he or she would like information regarding the visit to be sent to the patient's primary care physician. If he or she so desires, the information may be transferred, e.g., via hypertext link or other electronic connections, to the primary care physician in process 714. Any closing questions, comments and/or concerns of the patient, the patient's family or another health care practitioner are addressed and the visit is ended.

The described embodiments of the inventions are intended to be merely exemplary and numerous variations and modifications will be apparent to those skilled in the art. All such variations and modifications are intended to be within the scope of the present invention as defined in the appended claims.

What is claimed is:

1. A system for delivering medical examination, diagnosis, and treatment services from a health care practitioner to a patient over a network, the system comprising:
   a plurality of health care practitioner terminals, each of the plurality of health care practitioner terminals including a display device;
   a plurality of patient terminals in audiovisual communication over the network with any of the plurality of health care practitioner terminals;
   a call center in communication with the patient terminals and the health care practitioner terminals, the call center routing a call from a patient at one of the patient terminals to an available health care practitioner at one of the health care practitioner terminals, so that the available health care practitioner may carry on a two-way conversation with the patient and visually observe the patient; and
   a protocol database resident on a digital storage medium, accessible to each of the health care practitioner terminals, the protocol database containing a plurality of protocol segments such that a relevant segment of the protocol may be displayed in real time on the display device of the health care practitioner terminal of the available health care practitioner for use by the available health care practitioner in making an assessment of the patient.

2. A system according to claim 1, wherein the relevant segment of the protocol displayed in real time on the display device of the health care practitioner terminal includes an electronic link that establishes communication between the available health care practitioner terminal and a device of a third party.

3. A system according to claim 2, wherein the device of the third party is a device of one or more of a primary care physician, specialist, hospital, emergency room, ambulance service, clinic or pharmacy.

4. A system according to claim 2, wherein the electronic link is a hypertext link.

5. A system according to claim 1, further comprising a patient database accessible to each of the health care practitioner terminals for storing patient information.

6. A system according to claim 5, wherein the patient information is displayed on the display device of the health care practitioner terminal of the available health care practitioner.

7. A system according to claim 1, further including a medication database accessible to each of the health care practitioner terminals for storing medication information.

8. A system according to claim 1, wherein one or more of the patient terminals includes a telephone configured to cause a direct connection to the call center when the telephone receiver is lifted.

9. A system according to claim 1, wherein the protocol database is resident on a server that is in communication with each of the health care practitioner terminals.

10. A system according to claim 1, wherein each of the health care practitioner terminals includes a local storage device and the protocol database is replicated on the local storage device of one or more of the health care practitioner terminals.

\* \* \* \* \*